United States Patent [19]

Chan et al.

[11] Patent Number: 5,100,667

[45] Date of Patent: Mar. 31, 1992

[54] PROCESS FOR PELLETIZING INSECTICIDAL N-HYDROCARBOYL PHOSPHOROAMIDOTHIOATES AND PHOSPHOROAMIDODITHIOATES

[75] Inventors: Jim H. Chan, Martinez; Kent A. Hasse, El Sobrante; Roderick I. Satre, Point Richmond; James H. Trusler, Pleasant Hill, all of Calif.

[73] Assignee: Chevron Research and Technology Company, San Francisco, Calif.

[21] Appl. No.: 491,497

[22] Filed: Mar. 12, 1990

[51] Int. Cl.$^5$ ............................................. A01N 25/00
[52] U.S. Cl. ................................... 424/405; 424/409; 514/100; 514/113; 514/120; 514/128
[58] Field of Search ............... 514/120, 113, 100, 128; 424/409

[56] References Cited

U.S. PATENT DOCUMENTS

| | | | |
|---|---|---|---|
| 3,914,417 | 10/1975 | Magee | 514/120 |
| 4,544,553 | 10/1985 | Smolanoff | 514/113 |
| 4,560,682 | 12/1985 | Hiroki | 514/100 |
| 4,614,734 | 9/1986 | Smolanoff | 514/128 |
| 4,843,068 | 6/1989 | Hamaguchi | 514/188 |
| 4,892,732 | 1/1990 | Parconagian | 424/409 |

Primary Examiner—Thurman K. Page
Assistant Examiner—William E. Benston
Attorney, Agent, or Firm—Heller, Ehrman White & McAuliffe

[57] ABSTRACT

A method of making, without use of a solvent, insecticidal pellet compositions of N-hydrocarboyl phosphoroamidothioates and phosphoroamidodithioates is provided.

10 Claims, No Drawings

PROCESS FOR PELLETIZING INSECTICIDAL N-HYDROCARBOYL PHOSPHOROAMIDOTHIOATES AND PHOSPHOROAMIDODITHIOATES

The present invention is directed to a method of making, without use of a solvent, pelletized insecticidal compositions. In particular the present invention is directed to making pelletized insecticidal N-hydrocarboyl phosphoroamidothioates and phosphoroamidodithioates.

BACKGROUND OF THE INVENTION

Certain N-hydrocarboyl phosphoroamidothioates and phosphoroamidodithioates have high insecticidal activity. A particularly important commercial insecticide within these classes of compounds is the insecticide ORTHENE ®, which can be systemically taken up by a plant so that insects which feed and/or live on the plant are killed, in addition to those insects which directly ingest or are contacted by the insecticide. See U.S. Pat. Nos. 3,716,600, 3,845,172 and 3,914,417. ORTHENE ® is commercially produced as technical grade chemical of about 97 to 99.5% purity. One method of formulating technical grade ORTHENE ® for commercial use is to mix the technical grade powder with an anti-caking agent, such as fumed silica, and a wetting agent. The wetting agent is utilized to assist the wetting of silica (if present) and wet the ORTHENE ®, and the anti-caking agent is used to prevent agglomeration of the ORTHENE ® in its container.

The wetting agent is utilized to assist the wetting of the silica (if present) and to improve the spread-out of ORTHENE ® when it is applied to crops as a spray solution, or when applied as a dust, after exposure to moisture via rain, dew, or irrigation. The powdered commercial forms of ORTHENE ® are available in dilutions referred to as ORTHENE ® 90S, ORTHENE ® 75S, ORTHENE ® 50S, and in other commercial dilutions.

The powder form allows formulations of ORTHENE ® to relatively high concentrations, e.g., ORTHENE ® 90S. Other, lower concentrate formulations are targeted to discrete markets using a soluble powder signified as —xxS. In most cases, the application of ORTHENE ® xxS to the crop is via a water solution spray. The anti-caking agents, while promoting product flowability during the solution/mixing process, do not enhance the solution method of application. On the other hand, inherent to all powders, handling difficulties due to dust make this form of product less desirable than liquids and agglomerate forms. Furthermore, ORTHENE ® has a characteristically mercaptan odor (believed to be organothio compounds) which is compounded by the problems with dust.

ORTHENE ® is available in liquid form, which minimizes or eliminates airborne contamination due to dust. However, due to solubility and storage stability limitations of solutions, its concentration is limited to a maximum of 25%, the balance being solvent and adjuvants. ORTHENE ® in a liquid formulation has a solvent and packaging expense as well as a container disposal requirement that makes it less attractive to the consumer on the basis of price and empty container disposal requirements.

An agglomerate form of ORTHENE ® which also minimizes airborne contamination due to dust, has been constrained to dilute concentrations of ORTHENE ® applied to large particles by spraying and then dried, or as a dilute concentration of ORTHENE ® combined with binders and anti-caking agents to form agglomerates via processes known to those skilled in the art, such as, pan granulation, extrusion, fluid granulation, pelletizing. The concentration of ORTHENE ® via these methods has heretofore been limited to a concentration no greater than about 36% to 50%, with known commercial products typically no more than 5% ORTHENE. The limit on concentration of ORTHENE ® was due to the melt property of ORTHENE ® limiting the feasible operability of this form of product. Concentration of active ingredient is further limited by the ability of binding agents to form agglomerates, i.e. a minimum amount of any particular binding agent is required in order to meet physical properties of attrition resistance, crush strength and bulk density. In the case where liquid ORTHENE ® solutions were sprayed on agglomerates and then dried, the limitation of concentration was due to the practical wetting ability of the receiving agglomerate. Too much liquid applied would form a mud. At these low levels of ORTHENE ® concentration, commercial products are more costly to produce, and are not suitable for applications of ORTHENE ® made via solution spraying.

The ORTHENE ® xxS formulations have problems due to the anti-caking agent ingredients. Anti-caking agents are not soluble in water (the typical application spray solvent) or other normal solvents.

Due to their insolubility, they can settle in the applicator's spray tank. The settled anti-caking agents plug spray nozzles which detracts from the marketability of the ORTHENE ® xxS product line. This spray nozzle plugging problem can occur when ORTHENE ® xxS products are tank mixed with other commercial pesticides, which is a normal farming industry practice. While methods to minimize the occurrence of anti-caking agent settling have evolved, they require special procedures to avoid nozzle plugging conditions, which adds to the inconvenience of using ORTHENE ® xxS.

Furthermore, anti-caking agent segregates in the manufacturing process equipment during material handling procedures and forms insoluble bits of anti-caking agent which can cause nozzle plugging. This may lead to inconsistent application of the correct ORTHENE ® active ingredient.

Therefore, alternative forms to ORTHENE ® powders, that resolve problems characteristic of dusts are desired by both the manufacturer and the marketplace. One possible alternative to a powdered ORTHENE ® is in the form of a pellet: a cylindrically shaped solid. Pellets practically eliminate the dust problems and reduce the surface area-to-weight ratio which mitigates the odor problem.

However, currently available granular ORTHENE ®, as mentioned above, contain relatively small amounts of ORTHENE ®, typically no more than 5% active ingredient. Attempts to manufacture technical assay (approximately 97% active ingredient) granular ORTHENE ® from the dry ORTHENE ® technical powder have heretofore been unsuccessful. The anti-caking agents and binders needed to make the currently available granular ORTHENE ® add to product cost, can cause excess wear and tear on equipment, and by dint of being a major fraction of the product formula, require more bulk product than the concentrated powders in order to deliver effective amounts of ORTHENE ® to the protected crop.

Additionally, the anti-caking agents and binders used to form the currently available granular ORTHENE ® have the same water insolubility problem that the anti-caking agent has in ORTHENE ® powdered formulae. Because of that, commercial granular ORTHENE ® products are limited to use by direct application to the crop; i.e., placing individual ORTHENE ® granules on or around each plant, which is impractical for most commercial farming ventures.

It is thus an object of the present invention to provide pelletized forms of insecticidal N-hydrocarboyl phosphoroamidothioates and phosphoroamidodithioates containing high concentrations of insecticidal active ingredient.

It is a further object of the present invention to provide methods, without the use of a solvent, for making such pelletized compositions.

These and other objects of the invention will be apparent from the following description and from the practice of the invention.

SUMMARY OF THE INVENTION

The present invention provides a method for preparing insecticidal compositions without the use of a solvent, comprising pellets which contain as active insecticidal ingredients, a compound or mixture of compounds of the formula:

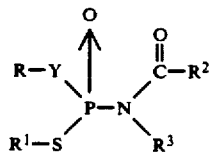

wherein R and $R^1$ individually are alkyl, alkenyl or alkynyl of up to 6 carbon atoms, $R^3$ is hydrogen or alkyl of 1-6 carbon atoms, $R^2$ is hydrogen, alkyl of 1-18 carbon atoms, cycloalkyl of 3-8 carbon atoms, alkenyl of 2-18 carbon atoms or alkynyl of 3-18 carbon atoms, and Y is oxygen or sulfur. The pellets are characterized by an attrition resistance of at least about 92%, a mean hardness of greater than about 1.5 lb-F and a bulk density of at least about 39 lb/ft$^3$ (about 0.63 gm/cc). The pellets are preferably made by extrusion. The concentration of the insecticidal ingredient in these pellets is in the range of about 50% to 95% a.i., with the most likely concentration of 90% a.i.

DESCRIPTION OF THE PREFERRED EMBODIMENTS

The active insecticidal ingredient of the pellets may be a compound or a mixture of compounds of the formula:

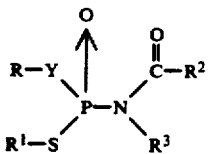

wherein R, $R^1$, $R^2$, $R^3$ and Y are as described hereinabove. Particularly preferred compounds are those in which R and $R^1$ are independently methyl, ethyl, allyl or alkenyl; $R^2$ is H or alkyl; and $R^3$ is hydrogen; and Y is oxygen. The most preferred compound is that in which R, $R^1$, and $R^2$ are methyl $R^3$ is hydrogen and Y is oxygen. Compounds of the above formula may be prepared as described in technical form in U.S. Pat. Nos. 3,716,600, 3,845,600 and 3,914,417 which usually provide compositions of about 97-98.5% purity. This technical grade insecticide will be mixed in a dry form with one or a mixture of surfactants, preferably comprising less than about 10% by weight of the total dry composition. Preferred surfactants include but are not limited to various nonionic polymeric surfactants which are known by the trade name "Pluronic ®" series and "Tetronic ®" series made by BASF.

The dry mixture may also contain inert diluents, such as ammonium sulfate, in an amount less than about 40% by weight of the total pellet composition, preferably 2% or less by weight of the total pellet composition.

Optionally, solid additives may be included in the dry mixture. Another additive may be anhydrous magnesium sulfate, in amount up to about 40% by weight of the total pellet composition, preferably 2% or less by weight. This serves as a dehydrating agent will absorb trace amounts of water present in the pellets to prevent hydrolysis of the insecticide.

Small amounts of deodorants may also be used as additives.

Small amounts of antifoam agent may be added to the formula.

Surfactants used in accordance with the present invention in order to form an extrudable solid composition, should be softenable within the temperature range of about 80° to 130° F. and have melting points greater than about 130° F. Such surfactants include the generic types alkyl or aryl alcohol ethoxylates. These surfactants are commercially available under the trade names Unithox TM (520, 580, etc.) made by Petrolite Chemical, Sellogen TM (Henkel) Pluronic ®, and Tetronic ® Surfactants, Tetronic ® block copolymers of propylene and ethylene oxides of ethylenediamine (BASF), Alkasurf TM, Alkatronic TM, Alkapol TM (glycols) sold by Alkaril Chemicals.

The particular surfactant used will depend in part on the intended use of the pellets. Those surfactants having an HLB range of 16 to greater than 20 will be substantially water soluble and therefore be usable in conventional mixing tanks used to distribute sprays. Pellets made from surfactants having an HLB lower than about 16 will have lower water solubility and will be useful, for example, in direct application on the plants or their environment for controlled release of the active ingredients of the pellet.

Particularly preferred surfactants for imparting high water solubility to the pellets are Unithox TM 480. Particularly preferred surfactants for imparting low solubility to the pellets are Unithox 520.

It will be appreciated that combinations of different surfactants may also be utilized to modify the solubility properties of the pellet as desired.

In the most preferred embodiment according to the present invention the pellets are made by forming a dry, extrudable mixture of the solid technical insecticide composition and surfactant, optionally containing other dry additives described above. The dry ingredients should be ground or provided in a powdered form. Usually about 10% or less by weight of the surfactant is used in the dry composition, preferably about 6% or less. In most instances a diluent such as ammonium sulfate will also be utilized, usually in an amount less than about 5% and usually around 1% by weight of the total composition. Preferably, no solvent is added to this composition. However, it is realized that many commercial versions of surfactants contain small amounts (typically about 2% by weight of the surfactant) of moisture. The presence of such moisture is not deleterious to the preparation of the pellet. The pellet may be further dried after manufacture, if desired.

While not intending to be limited by a particular theory, it is believed that the consistency of the dry mixture which leads to its extrudability is determined primarily by the plasticity of the surfactant at the extruding temperatures. Thus, surfactants which are softenable within a range of about 80° to 130° F. (which represents typical extruding temperatures), and which melt above 130° F., will provide the proper consistency to form an extrudable mixture.

As the extrusion product exits the extruding orifice, the product is cut to appropriate size, usually about 3 mm to 10 mm in length. Useful pellets will be extrudates of about 3 mm to 25 mm in length with diameters from about 1.5 mm to 7 mm. Spherical pellets are also useful having diameters of about 1 mm to 5 mm.

It will be readily apparent to those of ordinary skill in the art that other methods of making pellets may be utilized given the foregoing disclosure. The pellets according to the present invention will have an attrition resistance of at least 92% as determined by ASTM method D4058-87 on 5 mm (length)×2.38 mm (diam.) pellet. The mean hardness will also be greater than about 1.5 lb-F as determined by ASTM method D3313-88, and bulk density will be at least about 39 lb/ft$^3$ (about 0.63 gm/cc). These characteristics impart advantageous features, as discussed above, to the present invention as compared to powdered commercial ORTHENE ® compositions. In the present invention will exhibit improved odor control over commercial powdered formulations, such as ORTHENE ® 75S. Organothio odor is generally reduced by a factor at least 10 (ambient storage conditions) and thermal stability is improved over that of ORTHENE ® 75S.

Other advantages include reduction of production costs as compared to currently available pelletized ORTHENE ® which require the use of anticaking agents, such as fumed silica. The production costs of the pellets are also decreased with respect to wet extrudates (using solvents), since not only are the costs of the solvents avoided but also the requirement for drying equipment, and environmentally required ventilation equipment.

The following example is provided by way of illustration and is not intended to limit the invention in any way.

EXAMPLE

Sample pellets were made from ORTHENE ® technical powder, ammonium sulfate and various surfactants. The general procedure used was to grind the surfactant to about −20 mesh (Tyler). ORTHENE ® tech (powder) and technical ammonium sulfate were mixed for approximately five minutes in a Hobart mixer at speed No. 1. Then the surfactant was added and the mixture was mixed for about another five minutes at speed No. 1. This dry mixture was then used to make pellets in a laboratory scale California Pellet Mill equipped with an 2.38 mm diameter pellet stainless steel die, 127 mm/ID. Since some commercial surfactants contain a small amount of moisture, the mixtures are also assayed for moisture content. The bulk densities for the pellets were measured in an unpacked mode and in a packed mode in a graduated cylinder. The time required to dissolve these pellets in aqueous solution was then measured by dissolving five grams of the pellets in 500 ml. water samples at 25° C. and stirring at setting 4 on a Corning stir plate in a 600 ml. beaker with a magnetic stir bar. The time required to dissolve about 90% of the sample, and the time to dissolve 100% of the sample were recorded. As a standard the solubility test was also conducted on ORTHENE ® technical powder (assay 97.7%) and on pellets made from that powder (in a methylene chloride extruded mixture) to form 97SP pellets. The results show that the pellets made with a low HLB surfactant (samples 2 and 3) have much lower solubility in water than a conventional ORTHENE ® pellet (sample 7) or of ORTHENE ® technical powder (sample 6).

TABLE

| No. | ORTHENE (form) | PELLET SAMPLE (wt. %) SURFACTANT | AM. SULF. | MOIS-TURE | OR-THENE ASSAY | lb/ft3 BULK DEN. UN-PACKED | PACKED | TIME TO DISSOLVE 90% MIN. | SEC. | TIME TO DISSOLVE 100% MIN. | SEC. |
|---|---|---|---|---|---|---|---|---|---|---|---|
| 1. | 92.8 (90SP) | 6.2$^1$ | 1.0 | 0.32 | 92.1 | 43 | 45.4 | 3 | | 7 | 28 |
| 2. | 92.8 (90SP) | 6.2$^2$ | 1.0 | 0.22 | 91.18 | 40.6 | 41.9 | 3 | 30 | 6 | 45 |
| 3. | 92.8 (90SP) | 6.2$^2$ | 1.0 | 0.24 | 88.81 | 39 | 40.2 | 8 | | 11 | |
| 4. | 92.8 (90SP) | 6.2$^3$ | 1.0 | 0.16$^4$ | 89.97 | 36.7 | 38.1 | 1 | 50 | 2 | 30 |
| 5. | 76 (75 SP) | 6$^1$ | 18 | — | — | 45 | 46.6 | 3 | 20 | 8 | |
| 6. | 100 (TECH POWDER) | 0 | 0 | — | 97.7 | 18.7 | 25 | | 55 | 1 | 30 |
| 7. | 100 (97SP) | 0 | 0 | 0.18 | 97 | — | 42 | | 1 | 30 | 2 |
| 8. | 91.2 (90SP) | 5.2$^5$ | 2.0 | 0.45 | 91.2 | 37.5 | 39.6 | | 45 | 1 | 55 |

$^1$Unithox 580 (Petrolite, Inc.)
$^2$Unithox 520
$^3$Pluronic F-108 (BASF)
$^4$Extrusion sample made with 13% (wt.) methylene chloride. Data taken after solvent was evaporated.
$^5$Sellogen HR (Henkel)

What is claimed is:

1. A method for preparing water-soluble insecticidal pellets comprising i) a water-soluble insecticidal compound or mixture of water-soluble insecticidal compounds of from 50% to 95% the formula:

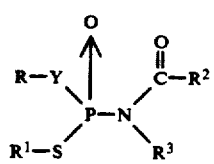

where R and R¹ individually are alkyl, alkenyl or alkynyl of up to 6 carbon atoms, R³ is hydrogen or alkyl of 1-6 carbon atoms, R² is hydrogen, alkyl of 1-18 carbon atoms, cycloalkyl of 3-8 carbon atoms, alkenyl of 2-18 carbon atoms or alkynyl of 3-18 carbon atoms, and Y is oxygen or sulfur; ii) a solid water-soluble surfactant that is softenable within the temperature range of about 80° to 130° F., comprising the steps of (a) forming an substantially dry extrudable mixture comprising said compound and said solid surfactant;

(b) forming said insecticidal pellets by extrusion of said dry mixture.

2. A method according to claim 1 wherein said dilutent comprises ammonium sulfate.

3. A method according to claim 1 wherein said surfactant comprises a said surfactant selected from the group consisting of alkyl and aryl alcohol ethoxylates.

4. A method according to claim 1 wherein R and R¹ are independently methyl, ethyl, allyl or alkenyl; R² is H or alkyl; R³ is hydrogen and Y is oxygen.

5. A method according to claim 4 wherein R, R¹, and R² are methyl; R³ is hydrogen.

6. A method according to claim 1 wherein said surfactant is characterized by an HLB of greater than about 16 and said pellets are substantially soluble in water.

7. A method according to claim 1 wherein said surfactant is characterized by an HLB of less than about 16 and said pellets release said insecticide at a controlled rate in the environment of a plant or soil.

8. A method according to claim 1 wherein said surfactant comprises less than 10% by weight of said mixture.

9. A method according to claim 2 wherein said ammonium sulfate comprises less than about 5% by weight of said mixture.

10. Water soluble insecticidal pellets made in accordance with any one of claims 1 through 3.

* * * * *

UNITED STATES PATENT AND TRADEMARK OFFICE
CERTIFICATE OF CORRECTION

PATENT NO.   : 5,100,667
DATED        : March 31, 1992
INVENTOR(S)  : Chan et al It is certified that error appears in the above-indentified patent and that said Letters Patent is hereby corrected as shown below:

In Column 5, Line 36: "In the present" should read -- In general pellets of ORTHENE® made in accordance with the present --

In Column 8, Line 21: "through 3" should read -- through 9 --

Signed and Sealed this

Twenty-fourth Day of August, 1993

Attest:

Attesting Officer

BRUCE LEHMAN
Commissioner of Patents and Trademarks